(12) United States Patent
Friedman et al.

(10) Patent No.: US 8,374,886 B2
(45) Date of Patent: Feb. 12, 2013

(54) COMPUTER BASED CLINICAL LABORATORY ORDERING AND REPORTING SYSTEM WITH EMBEDDED CONSULTATION FUNCTION

(75) Inventors: Bruce A. Friedman, Ann Arbor, MI (US); Francis Michael Walsh, Toledo, OH (US)

(73) Assignees: Francis Michael Walsh, Bay Harbor, MI (US); Bruce A. Friedman, Ann Arbor, MI (US); Atlas Development Corporation, Calabasas, CA (US)

( * ) Notice: Subject to any disclaimer, the term of this patent is extended or adjusted under 35 U.S.C. 154(b) by 3944 days.

(21) Appl. No.: 10/605,125

(22) Filed: Sep. 10, 2003

(65) Prior Publication Data
US 2005/0055240 A1 Mar. 10, 2005

(51) Int. Cl.
*G06Q 10/00* (2012.01)
(52) U.S. Cl. .......................................................... 705/2
(58) Field of Classification Search .................. 705/2, 4, 705/7; 706/2; 395/203, 924; 379/202.01; 600/300
See application file for complete search history.

(56) References Cited

U.S. PATENT DOCUMENTS

| 5,692,220 | A * | 11/1997 | Diamond et al. | 600/368 |
| 5,737,539 | A * | 4/1998 | Edelson et al. | 705/3 |
| 5,819,242 | A * | 10/1998 | Matsuoka et al. | 706/2 |
| 5,823,948 | A * | 10/1998 | Ross et al. | 600/300 |
| 2002/0071540 | A1 * | 6/2002 | Dworkin | 379/202.01 |
| 2002/0099586 | A1 * | 7/2002 | Bladen et al. | 705/7 |
| 2003/0069759 | A1 * | 4/2003 | Smith | 705/3 |

OTHER PUBLICATIONS

Atlas Medical, Inc. Atlas LabWorks (www.atlasdev.com) web pages dated Aug. 2, 2002.*
Publication by Atlas LabWorks, *Your Competitive Advantage*, © 2003, Atlas Development Corporation.

* cited by examiner

*Primary Examiner* — John Pauls
(74) *Attorney, Agent, or Firm* — Jerome R. Drouillard

(57) ABSTRACT

A system for facilitating the provision of clinical laboratory services includes an order entry subsystem for submitting patient test requests to a laboratory by means of a networked terminal, an online data storage subsystem, a triage subsystem for comparing test results with predetermined reference ranges, and a reporting-consulting subsystem for use by an embedded consulting physician to generate a consultative report which is communicated by a networked terminal to the person submitting the test request.

5 Claims, 3 Drawing Sheets

COMPUTER BASED CLINICAL LABORATORY ORDERING AND REPORTING SYSTEM WITH EMBEDDED CONSULTATION FUNCTION

BACKGROUND OF INVENTION

FIELD OF THE INVENTION

The present invention relates to a computer-based system for providing clinical laboratory services, with test results being processed through a variety of subsystems and concluding with a consultative subsystem under the control of a laboratory-based consultant utilizing disease-specific templates to generate interpretive test reports based upon one or more test results.

Disclosure Information

The provision of clinical laboratory testing generally follows a model which has evolved over decades. According to this prevailing model, a physician, who may be a primary care physician ("PCP") such as a pediatrician, an obstetrician-gynecologist, an internist, or a family practitioner, or another type of specialist such as a cardiologist or oncologist, orders one or more tests from a clinical laboratory in the process of evaluating a patient. All such physicians or other persons ordering laboratory tests and receiving test results and consultative services via the current system are hereinafter referred to collectively as "clinicians".

Having been examined by a clinician, the patient is direct to present himself or herself to a laboratory-managed blood-drawing station, or more generally, a patient service center, wherein biologic samples such as blood or other bodily fluids such as urine or saliva are obtained from the patient using established test procedures. These biologic samples are then processed within the clinical laboratory using various analytic instruments and test procedures. Then, the results generated by these instruments and procedures are mailed, or faxed, or couriered to the clinician's office for review. In urgent cases, results may be provided by phone, or even by an electronic message such as email or by an alphanumeric pager. In certain cases, the patient will be subjected to other types of tests or specialized examinations such as those utilizing various types of imaging.

After the clinician who initially ordered the test reviews the results, the clinician must then decide how the patient will be subsequently managed. Test results may be used for diagnostic purposes or for monitoring progress when a disease is being treated. In the event, however, that the clinician has a question regarding the interpretation of the test results, a difficulty may arise because it is often inconvenient, if not very difficult, for the clinician to confer over the telephone or in person with the laboratory-based physician consultant or other laboratory scientist about the case. Another difficulty associated with known systems for providing clinical laboratory consultative services arises from the fact that even when laboratory-based consultants are available, they may not have ready access to the longitudinal historical record of test results pertaining to the patient from previous hospital encounters. And, the consultant will almost certainly not have access to test results stored in the clinician's office computer systems. Moreover, if the consultative encounter between the clinician and the laboratory-based consultant is not ordered and documented in a formal manner, the patient's insurer will not render payment to the laboratory consultant for the consultative services provided.

In most cases, laboratory information systems, which are the current transaction engine for the clinician customers of clinical laboratories, do not take advantage of "public" network infrastructures like the Internet. Although laboratory portal software systems, such as that currently available from Atlas Medical, Inc. are known in which test orders may be placed over the Internet and results received in the same manner, such known systems clearly lack the laboratory medicine consultative capabilities which are required to consistently provide more than a rote listing of numerical test results or terse narrative reports, to a busy clinician who may have little free time to perform the analysis and research needed to interpret certain laboratory test results, particularly those that are more complex.

A clinical laboratory transaction with an embedded consultation function according to the present invention solves the problems inherent with known laboratory systems by providing accurate, on-line ordering, processing, reporting of results, interpretation, and reflexive testing. The consultation function, and indeed, the consultants themselves, according to the present invention are said to be "embedded" because the consultants, who are associates of the laboratory itself, are an integral component of the testing and reporting process. The embedded consultants are wholly dedicated to the provision of laboratory testing services; it is not expected that they would maintain a practice. Rather, the consultants will solely serve the professional needs of the test-ordering clinicians and therefore will not be in competition with the clinicians for patients.

The present method and system provides test results and other relevant clinical information which are retrieved by the system itself for use by embedded clinical consultants who form an integral part of the inventive clinical laboratory transaction system.

SUMMARY OF INVENTION

A system for providing clinical laboratory transaction and diagnostic services includes an order entry subsystem for submitting orders for diagnostic tests to the performing laboratory. As used herein, the term "system" includes, without limitation, a network of computers utilized to perform various functions described in this specification. A laboratory receiving the orders fulfills the orders using analytic instruments located in the laboratory, thereby generating test results which are received, recorded and stored in a database, termed a "data storage subsystem" herein. A triage subsystem then compares the test results with predetermined reference range (i.e., normal) values. The triage subsystem culls out abnormal test results for subsequent review by an embedded consultant, as well as those normal results that are significant in light of a previous patient history of abnormal results of the same type stored and accessible in the data storage subsystem. All test results, whether normal or abnormal, and accompanied by a consultative report, when such a report is indicated, are communicated to the test-ordering clinician via a reporting-consulting subsystem.

The reporting-consulting subsystem deals with test results lying outside prescribed reference ranges, as well as normal test results for patients with a history of abnormals of the same type. This subsystem provides at least one template for selection by a consultant physician ("consultant"). The consultant selects an appropriate template to generate a consultative report having a content which is largely driven by the array of abnormal test results.

According to another aspect of the present invention, the reporting-consulting subsystem will provide the consultant generating the consultative report with access to additional clinical databases in addition to access to both new and the historical test results for the patient. Such additional clinical databases, include, but are not limited to, for example, a radiology information system, a pharmacy information system, and a clinical data repository of the hospitals to which the patient may have been admitted for inpatient care and managed by the very same clinician now seeing the patient in an office setting.

According to another aspect of the present invention, a reporting-consulting subsystem may further include a feature whereby the clinician receiving a consultative report, having read the report, and having questions about either the test results themselves or the consultative report accompanying the results, can push a button on a web-based result reporting system which rapidly places the clinician into telephone contact with a consultant, frequently the consultant who initially generated the consultative report sent to the clinician. This telephone link is initiated by a server subsystem which has access to the telephone numbers of both the clinician and the consultant.

According to another aspect of the present invention, the present laboratory testing system, and more specifically, the reporting-consulting subsystem, further comprises a routine for downloading archival test results for patients and a subroutine for predicting future test results based at least in part upon previously stored test results for each particular patient.

According to another aspect of the present invention, the present laboratory testing system, and more specifically, the reporting and consultation subsystem, further comprises a system whereby the consultant can recommend an additional round of more specific or sensitive tests, based on positive results obtained during the previous round of testing but using the previously drawn blood samples for reasons of patient convenience. Such testing is referred to as "reflexive testing." The present invention facilitates such reflexive testing in a manner not previously available because when the consultant who drafted the consultative report recommends such follow-on testing, this recommendation is rapidly transmitted to the clinician whose test order is required by payers for a new round of testing. The test-ordering subsystem of this invention thus facilitates the electronic ordering of the new round of testing. The latter serves the interests of patients, clinicians, and payers alike because it is a more efficient way of arriving at a diagnosis by reducing the time for completing testing cycles.

According to another aspect of the present invention, the triage subsystem further includes an alert subsystem for establishing a time-based test performance sequence, with the alert subsystem contacting a clinician or other patient care representative in the event that subsequent test performance is required according to a specified time interval. The alert subsystem may also be employed to notify the test-ordering clinician or the clinician's office staff if the test order is incomplete or incorrect, or in the further event that the test results indicate that rapid intervention is required. The automation of such alerts increases the quality of patient care by decreasing the response time for such correction or intervention.

According to another aspect of the present invention, interfaces are installed between the present laboratory test ordering, reporting, and consulting system and the various computer systems installed in the clinicians' offices, which are termed "practice management systems" (PMSs). Clinicians use PMS to maintain financial records and also to create an office-based clinical electronic medical record (EMR). The outward-bound interface from the clinician's office uploads to the laboratory such data as patient demographic information, which facilitates office test ordering by pre-entering patient demographic information into the appropriate data fields in the electronic test order. The inward-bound or down-link aspect of the interface from the laboratory system to the PMS allows the clinicians' office-based electronic medical records to maintain a record of pending laboratory test orders and also the integration of the results of completed tests into the office clinical record.

According to another aspect of the present invention, the templates included within the reporting-consultation subsystem incorporate interpretative data for use by the clinician and the consultant, such as patient-specific archival data, tabular data, and graphical data illustrating data trends over time.

According to another aspect of the present invention, the embedded consultant's report will be sent to a networked terminal designated by the clinician. This terminal would very likely be located within the clinician's office. In most cases, when a consultative report is communicated to the clinician, the report itself will provide sufficient guidance and advice to the clinician. In some cases, however, the clinician will require direct contact with the consultant. The aforementioned subsystem that enables the establishment of a telephone linkage between the clinician and the consultant will serve this purpose. For more elaborate multi-party consultative requirement, the present invention allows the clinician to initiate an Internet-enabled audio conference including the laboratory consultant and other professional colleagues such as other medical specialists participating in the diagnosis and treatment of the patient.

According to another aspect of the present invention, a method for providing diagnostic laboratory services to office-based clinicians includes the optional step of submitting an order to a laboratory for a diagnostic test by means of a networked terminal device such as a personal computer (PC) running as either a thick or thin client, portable hand-held networked device such as a PDA or mobile phone with Internet access and running a browser, or other similar devices, followed by the steps of processing, or managing a patient to a fulfill a test order, thereby generating test results, and loading the test results into a data storage subsystem. As used herein, the term "thick client" means a personal computer running multiple applications and having a local data storage capability. And, a "thin client" is a personal computer running a browser that connects to a server remotely running the application and remotely storing the test results.

A method according to the present invention continues with the step of using a triage subsystem to compare the test results contained within the data storage subsystem with reference range (i.e. normal) values. In the event that the test results lie within the normal range for that particular test, the test results will be transmitted directly back to the test requestor using a networked terminal device or other front end hardware which may be housed within the reporting-consulting subsystem. In the event, however, that the test results lie outside the normal range, the test results will also be transmitted by a networked terminal device to a consulting physician via a reporting and consultation subsystem. The consultant will use at least one report template contained within the reporting-consulting subsystem to generate a consultative report. This report will be communicated to the clinician by means of a networked terminal device.

The present method further includes the steps of requesting test orders and performing additional reflexive tests, if such testing is indicated. Reflexive testing may be recommended by the laboratory consultant in the consultative report. Such additional test ordering is facilitated by the fact that the networked PC in the clinician's office will support both electronic test ordering and results reporting.

The present method further includes the step of alerting the test-ordering clinician via a networked terminal, a text pager, or email that test results and a consultation report are awaiting his/her review.

It is an advantage of the present invention that the consultative report which is prepared as part of the inventive method and system will be able to assist the clinician in the interpretation of abnormal results and the subsequent development of a therapeutic regimen for the patient under care that may not be readily ascertainable without time intensive study. This will help to avoid the problem of misdiagnosis and lead to a higher quality of healthcare and increased patient safety.

It is another advantage of a system and method according to the present invention that the present triage engine will provide an alert, as described above, to both the clinician and the embedded consultant in the event that a patient's test results, although nominally in the normal range, in fact indicate that the patient's condition has changed because the results are contrary to a previously recorded trend.

It is another advantage of the present invention that the present system and method provide guidance for the clinician in complex cases where additional information may be required to assist the clinician in the interpretation of test results or in planning therapy. In order to provide such assistance, the consultative reports will frequently contain URLs that provide hot-links to medical web sites containing additional sophisticated information about diagnosis and treatment.

It is another advantage of the present invention that the present system and method provide a ready mechanism for the clinician to obtain further individualized consultation on a timely basis.

It is a further advantage of the present invention that web-based ordering and reporting of test results allows busy physicians to time shift so as to be able to order tests, review test results, and review comprehensive consultative reports on a 24/7 basis, wherever the clinician has Internet access.

It is a further advantage of the present invention that the triage subsystem culls out either abnormal or otherwise notable results, thereby allowing the embedded consultants associated with the system to review only cases which are truly meritorious of further attention and a consultative report.

The present system and method offers the further advantage of allowing clinicians to pursue a reflexive test ordering strategy, but only when such testing is truly indicated by prior abnormal or otherwise remarkable results, as interpreted by the superior system inherent in the present laboratory method, thus increasing efficiency by performing the most appropriate and relevant tests more quickly and also satisfying payers that the clinician is actively participating in the test ordering process.

It is a further advantage of the present system that additional reflexive testing may be performed using original specimens collected from a patient because of the relative speed and ease offered to the clinician seeking additional testing, while avoiding additional venepunctures of the patient.

It is a further advantage of the present system that alerts are provided so that the clinician requesting a test will be notified at some future time when recommendations for further testing, contained in a consultative report, if any, come due. The clinician can then immediately make use of the order entry feature of the present system to order the recommended new tests.

It is a further advantage of the present system that the consultative reports generated by the embedded consultant may be transmitted to the requesting physician with a digital signature sufficient to meet regulatory requirements, such as those attendant the Health Insurance Portability and Accountability Act ("HIPAA").

It is a further advantage of the present system that this system includes a billing routine in software, for invoicing the patient's insurer by means of an invoice bearing an AMA CPT code.

Other advantages, as well as features and objects of the present invention, will become apparent to the reader of this specification.

DETAILED DESCRIPTION

Figure 1:
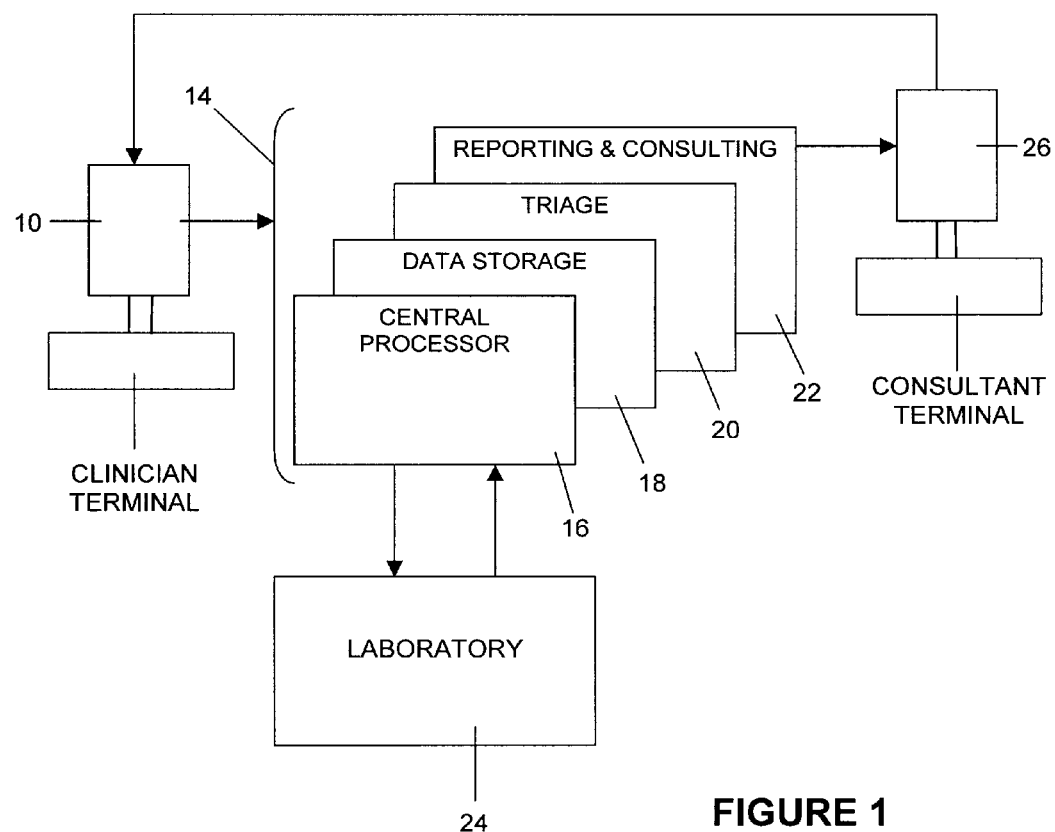
FIG. 1 is block diagram illustrating component parts of a clinical laboratory ordering and reporting system with embedded consultation according to the present invention.

As shown in FIG. 1, a clinician terminal is used to submit an order to the present system shown at 14. System 14 includes central processor 16, data storage subsystem 18, triage subsystem 20 and reporting-consulting subsystem 22. Central processor 16 transmits a test request to laboratory 24, which manages the patient to obtain test results, either by collecting biologic samples and processing them, or by performing some other diagnostic test, such as various tests including imaging. As described more fully below, results lying outside of a predetermined normal reference range are triaged by triage subsystem 20 and reported to consultant terminal 26 by means of reporting-consulting subsystem 22. Reporting-consulting subsystem 22 is multifunctional. Thus, reporting-consulting subsystem 22 reports both normal results to the clinician, usually without a consultative report, and abnormal results, usually accompanied by a consultative report. As set forth more fully below, subsystem 22 also selects an appropriate template for a consultative report in the event that the test results are remarkable. Finally, subsystem 22 communicates completed consultative reports to the requesting clinician.

A consultant working at terminal 26 completes a consultative report which is transmitted via the Internet or through some other networked terminal device to clinician terminal 10. Those skilled in the art will appreciate in view of this disclosure that each of the component subsystems of the present system, such as data storage subsystem 18, triage engine 20, and reporting-consulting subsystem 22 may be either distributed or housed at a single location. This distributed (i.e., remote from where the information is generated) form of access to an application and data storage is commonly referred to as an application service provider (ASP) model.

Figure 2A:
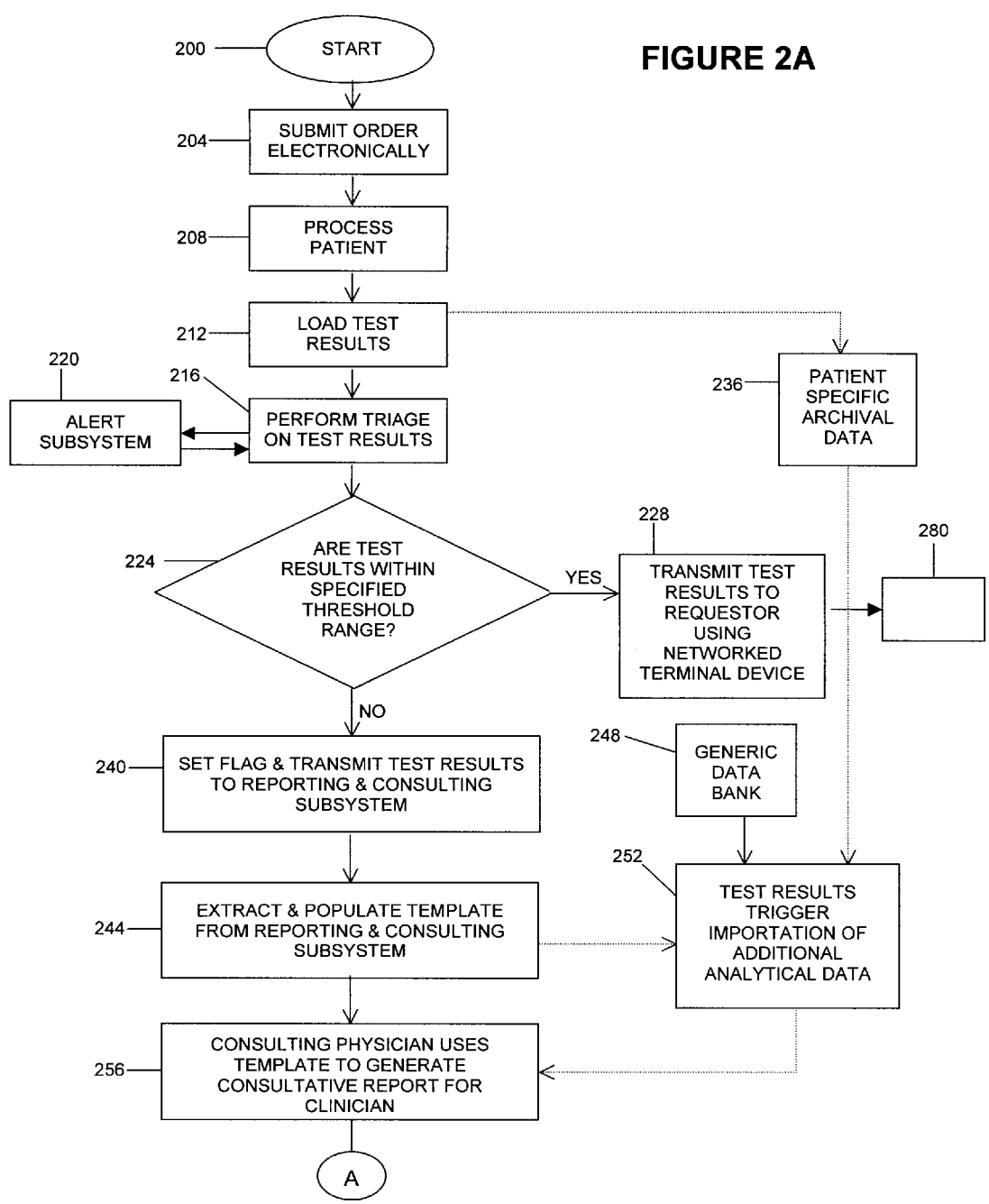
FIGS. 2A and 2B are flowcharts illustrating operation of a clinical laboratory ordering and reporting system according to the present invention.
Figure 2B:
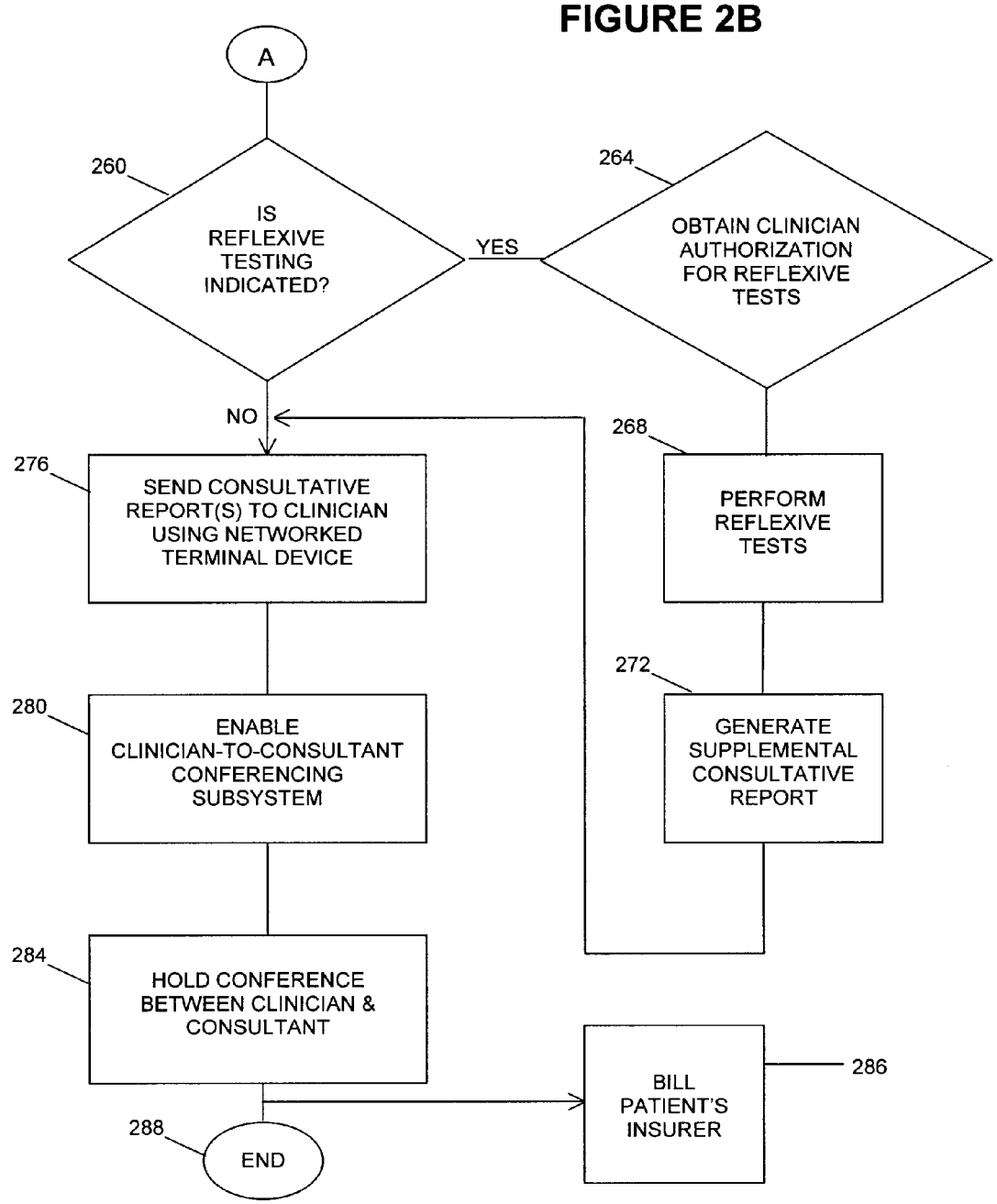

As shown in FIG. 2, a process according to the present invention starts at block 200. At block 204, the clinician electronically submits an order for a laboratory test, This order may be submitted by means of a clinician-office-based "thick" terminal (client) having both the application and data stored locally on a PC, or a "thin" terminal (client) without a database of patient data, but having the capability to access the application and data from a remote server using a browser stored on the PC. Alternatively, the clinician could submit an order by other types of devices such as a networked personal digital assistant (PDA) running a browser with Internet access.

The laboratory test order is received by system 14, which transmits the order to test-performing laboratory 24. Those skilled in the art will appreciate in view of this disclosure that system 14 could be housed either on the premises of laboratory 24, or elsewhere. In any event, after the order is submitted electronically at block 204, the routine moves to block 208 wherein the patient is managed by medical laboratory 24 so as to generate test results. This step may involve collecting a biologic specimen from the patient, which could be a blood sample collected by phlebotomy, with the blood sample being analyzed by laboratory instruments. Patient management also encompasses other critical processes such as the assuring the correct identification of the specimen(s) and processing financial information relating to payment for the laboratory services.

Those skilled in the art will appreciate in view of this disclosure that many other types of tests such as noninvasive tests employing various types of imaging, as well as invasive tests such as tissue biopsies could be processed and the results reported using a method and system according to the present invention.

The test results are sent by laboratory 24 to system 14. More specifically, the results are sent to data storage subsystem 18 shown in FIG. 1. Then the routine moves to block 216, where the test results are uploaded from data storage subsystem 18 by triage subsystem 20 to allow triage to be performed on the test results. As used herein, the term "triage" means that the results are compared with predetermined reference ranges to determine which of the test results are abnormal. Triage subsystem 20 preferably comprises a software filter which is populated with ranges for all anticipated laboratory test results. In essence, triage subsystem 20 is rule-driven, with the rules being based upon knowledge of normal test ranges and, in a more sophisticated manner, knowledge about how groups of test results are altered on the basis of disease conditions. Triage subsystem 20 also incorporates the capability of scanning previous test results for a patient. This is useful because a patient with currently normal test results but with a history of prior abnormal results may require a consultation, either because of apparent improvement of a clinical condition, or sometimes the suggestion that the current result may represent an inaccurate result. Because the triage subsystem flags results demanding closer scrutiny, the consultant need not spend time either reviewing or commenting on the multitude of results which are unremarkable. On the other hand, results that are flagged as remarkable for any reason by the triage engine, are forwarded to an embedded consultant.

The results of the comparison at block 216 are imported into block 224, wherein a question is asked regarding the comparison. If the test results are generally within normal values, reporting-consulting subsystem 22 transmits the test results directly to the test requestor at block 228, preferably through the use of a networked terminal device. After block 228, the routine shuttles to block 280, where a clinician-to-consultant conferencing subsystem is enabled. This step is more fully explained below.

If the answer to the question posed at block 224 is "No", the test results are not within the specific test reference range, and the routine moves to block 240, wherein triage subsystem 20 sets an abnormal results flag and transmits the test results bearing the flag to reporting-consulting subsystem 22. The abnormal will generally be transmitted to the clinician without a consultative report at this time, for possible action on his/her part. Abnormal results will generally trigger the creation of a consultative report which will usually be generated quickly enough that it can be transmitted to the clinician with the results themselves. Repetitive abnormal results will frequently not justify the creation of a consultative report because, in such cases, the clinician is aware of the abnormality and is treating the patient appropriately. In such a case the test repetition is used for patient monitoring purposes rather than for diagnostic purposes.

At block 244, the abnormal results flag set by triage subsystem 20 triggers reporting-consulting subsystem 22 to extract and populate a template selected by the consultant from a library of such templates located within subsystem 22. In some cases, the test results will trigger the importation of additional analytical data from diverse sources at block 252. These data could include, for example, comparative data such as epidemiological data, drawn from a generic data bank, that would be of value in interpreting or assessing the disease of the patient under consideration, as shown at block 248, or could be patient-specific archival data drawn from block 236 which receives results on demand from data storage subsystem 18. The additional data imported into reporting system 22 at block 252 may include not only tabular data but also graphically presented data, both generic and patient-specific. An example of this type of data could include annotated digital images from a surgical pathology report representing tissue removed from the patient at the time of biopsy or surgical resection of a tumor, for example.

One of the most important aspects of the present invention occurs at block 256 wherein the consulting physician uses the template populated at block 244 and, where appropriate, augmented at block 252, to help generate a consultative report for the clinician. The use of a template format provides a number of distinct advantages to the consultant: it provides an efficient means for the consultant to generate a sophisticated report very quickly; it also provides the clinician receiving the document with both a record of the test results and a sophisticated guide to its treatment; and, it provides the clinician with access to other reference and teaching materials.

It is readily seen that the template is not a mere outline; it is a powerful tool having linked Internet references (i.e., URLs), and, where appropriate, graphical presentation of the individual patient's test results. These templates will be created by medical experts in the various specialties. The templates will be updated frequently to assure their relevance, usefulness, and currency. In order to generate a disease-specific report, the most relevant and appropriate pre-developed disease-specific template is selected by the consultant and the patient's test results are made to flow into the appropriate fields in the template. The template includes the option for the consultant to add free-text comments to the report to personalize the report beyond the limits of the template that is used as the base for the report. The template also includes, when necessary and relevant, URLs for additional Internet resources so that the clinician receiving the report can review additional diagnostic and treatment information at various web sites.

The power and flexibility of the results-driven, template-based reporting-consulting subsystem yield time savings sufficient to render the embedded consultation capability an affordable feature of the present system. Another advantage of the present system resides in the fact that the consultant's time and effort expended in the creation of the consultative report will readily be compensated because the laboratory will be permitted to bill the patient's insurer under the appropriate American Medical Association ("AMA") billing CPT code covering laboratory consultation. To accommodate billing requirements, and in keeping with the format of any medical consultative report, the consultant will affix an electronic signature, preferably in a digital format, to each report. This signature may be either the name or the consultant, or a code or other device. Under the Uniform Electronic Transactions Act or the Electronic Signatures in Global and National Commerce Act ("E-Sign"), such electronic signatures have the same legal effect as a handwritten signature. As a result, the need for a paper record is eliminated. Should the need arise, the clinician receiving the report has the option of generating a hard copy from his/her PC.

Use of an appropriate AMA CPT code a digital signature in connection with the consultant's report will assure that the record created by the consultant is compliant with the Health Insurance Portability and Accountability Act ("HIPAA"). As used herein, the term "digital signature" means an electronic signature based upon cryptographic methods of originator authentication, computed by using a set of rules and a set of parameters so that the identity of the signer and the integrity of the data can be verified. Further, a HIPAA-compliant digital signature must implement features allowing for message integrity, nonrepudiation, and user authentication. The present system provides for integration of digital signatures into the transaction, while complying with the HIPAA electronic signature standards, and many aspects of the overall HIPAA regulatory scheme with regard to security.

Having performed an initial evaluation and having drafted the consultative report at block 256, the consultant will be prompted to determine at block 260 whether reflexive testing is indicated. Reflexive testing is the ordering of subsequent and more specific tests based on abnormal results from the first round of testing. The value of this process is that the subsequent tests can frequently be performed using the original biologic samples. By reducing the time required for each testing cycle, reflexive testing may promote a more rapid diagnosis.

A critical advantage of the present system is that the Internet-based (i.e., web-enabled) communication platform offered by the system allows the consultant to more easily maintain an effective and inexpensive communication linkage with the clinician, so as to obtain the required permission from the clinician to conduct the additional reflexive testing. The lack of such efficient two-way communication between the clinical laboratory and the clinician has proven to be a significant barrier to the adoption of reflexive testing in the past, despite its obvious advantages in efficiency and quality of care. Moreover, as noted above, the speed of the communication provided by the present system will often allow the original biologic specimen taken from the patient to be used for reflexive testing, which means that patient convenience is increased.

At block 264, clinician authorization is sought for reflexive tests before such tests are performed at block 268, followed by the generation of a supplemental consultative report at block 272. In any event, at block 276, the consultative report(s) are sent to the clinician. Thereafter, at block 280, a clinician-to-consultant conferencing system is enabled. This conferencing system, which is located within system 14, allows the clinician to request and schedule a net meeting with both an embedded consultant and, for more complex cases, one or more specialized expert(s) such as a cardiologist or oncologist. As noted above, the present system also accommodates and automates the provision of a point-to-point telephone conference between the clinician and the consultant, which may be simpler than an Internet-based conference. After arranging the conference, the conference is actually held at block 284 between at least the clinician and the embedded consultant. The patient's insurer is billed for the consultation at block 286, and the process concludes at block 288.

The present system and method may be configured to include test alerts. Test alerts, as the name implies, are messages, sent to the test-ordering clinician, which indicate that an action needs to be taken, such as a follow-up test order, at some time interval following the receipt of test results which were either suspicious or borderline. The need for such follow-up testing will frequently be included in the consultative lab report. However, the clinician receiving such a recommendation may fail to act on the recommendation. The reporting system will record such future testing recommendations and deliver an electronic alert in the clinicians' electronic in-box in proximity to the day that the repeat test or follow-on test should be ordered.

Although the present invention has been described in connection with particular embodiments thereof, it is to be understood that various modifications, alterations, and adaptations may be made by those skilled in the art without departing from the spirit and scope of the invention set forth in the following claims.

The invention claimed is:

1. A method for providing clinical laboratory services, comprising the steps of:
submitting an order to a laboratory for a diagnostic test by means of a networked terminal device;
managing a patient to fill said test order, thereby generating test results;
loading said test results into a data storage subsystem;
comparing said test results contained within said data storage subsystem with predetermined reference range values, and thereafter causing the test results to be transmitted directly to the test requestor, using a networked terminal device, in the event that the test results are within said reference range, but causing the test results to be transmitted by a networked terminal device to a consulting physician via a consultative reporting-consulting subsystem in the event that the test results are outside said reference range;
receiving said test results lying outside of said reference range in a reporting-consulting subsystem, and using said reporting-consulting subsystem to provide at least one selectable report template;
using said report template and said consulting physician to generate a consultative report based at least in part upon the test results; and
communicating said consultative report, bearing an electronic signature, to the test requester by means of a networked terminal device.

2. A method according to claim 1, wherein said report template incorporates at least one importable additional data source for providing test result driven data for generating said consultative report.

3. A method according to claim 1, further comprising the step of linking the test requestor to a conferencing system by means of a networked terminal device, for scheduling a conference with the consultant who generated said consultative report.

4. A method according to claim 1, further comprising the step of linking the test requestor to a conferencing system by means of a networked terminal device, for scheduling a net meeting with at least the consultant who generated said consultative report.

5. A method according to claim 1, further comprising the step of billing the patient's insurer for the time expended by the consulting physician to analyze said test results and to draft said consultative report.

* * * * *